US010352883B2

(12) United States Patent
Krapf et al.

(10) Patent No.: US 10,352,883 B2
(45) Date of Patent: Jul. 16, 2019

(54) HAND-HELD MEASURING APPARATUS AND METHOD FOR THE OPERATION THEREOF

(71) Applicant: Robert Bosch GmbH, Stuttgart (DE)

(72) Inventors: Reiner Krapf, Filderstadt (DE); Felix Kurz, Steinheim (DE)

(73) Assignee: Robert Bosch GmbH, Stuttgart (DE)

( * ) Notice: Subject to any disclaimer, the term of this patent is extended or adjusted under 35 U.S.C. 154(b) by 128 days.

(21) Appl. No.: 15/507,280

(22) PCT Filed: Aug. 11, 2015

(86) PCT No.: PCT/EP2015/068414
§ 371 (c)(1),
(2) Date: Feb. 28, 2017

(87) PCT Pub. No.: WO2016/037783
PCT Pub. Date: Mar. 17, 2016

(65) Prior Publication Data
US 2017/0261444 A1 Sep. 14, 2017

(30) Foreign Application Priority Data
Sep. 12, 2014 (DE) .......................... 10 2014 218 364

(51) Int. Cl.
*G01V 3/00* (2006.01)
*G01N 24/08* (2006.01)
(Continued)

(52) U.S. Cl.
CPC ........... *G01N 24/082* (2013.01); *G01N 24/08* (2013.01); *G01N 24/081* (2013.01);
(Continued)

(58) Field of Classification Search
CPC .............. G01R 33/3808; G01R 33/441; G01R 33/3415; G01R 33/36; G01R 33/3628;
(Continued)

(56) References Cited

U.S. PATENT DOCUMENTS

2014/0009170 A1    1/2014  Troxler
2014/0070810 A1*   3/2014  Robert ............... G01R 33/3628
                                                    324/322
2014/0084927 A1    3/2014  Walsh et al.

FOREIGN PATENT DOCUMENTS

CN        201719247 U      1/2011
DE    10 2008 055 196 A1   7/2010
(Continued)

OTHER PUBLICATIONS

International Search Report corresponding to PCT Application No. PCT/EP2015/068414, dated Oct. 29, 2015 (German and English language document) (8 pages).
(Continued)

*Primary Examiner* — Rodney E Fuller
(74) *Attorney, Agent, or Firm* — Maginot, Moore & Beck LLP

(57) ABSTRACT

A mobile measuring apparatus for nondestructively determining a material measurement value that relates to a material property of a workpiece comprises a housing in which at least a first sensor device and a second sensor device are located, a control device, an evaluating device, and a device for the supply of energy to the measuring apparatus. The first sensor device has a nuclear magnetic resonance sensor and the second sensor device has a sensor based on dielectric and/or resistive methods. Information about the material property of the workpiece, in particular moisture present in the workpiece, is obtained by evaluating a measurement signal provided by the first sensor device, which information is intended for the optimized control of the second sensor device and/or optimized evaluation of measurement signals provided by the second sensor device.

20 Claims, 5 Drawing Sheets

(51) Int. Cl.
   *G01R 33/38* (2006.01)
   *G01S 15/02* (2006.01)
   *G01S 13/02* (2006.01)
   *G01S 13/86* (2006.01)
   *G01S 13/88* (2006.01)
   *G01S 15/88* (2006.01)
   *G01R 33/34* (2006.01)

(52) U.S. Cl.
   CPC ... *G01R 33/34007* (2013.01); *G01R 33/3808* (2013.01); *G01S 13/0209* (2013.01); *G01S 13/86* (2013.01); *G01S 13/88* (2013.01); *G01S 15/025* (2013.01); *G01S 15/88* (2013.01)

(58) Field of Classification Search
   CPC .... G01R 33/3664; G01N 22/00; G01N 22/04; G01N 22/081
   USPC .......................................................... 324/309
   See application file for complete search history.

(56) References Cited

FOREIGN PATENT DOCUMENTS

EP           2 182 390 A2    5/2010
WO           00/04493 A1     1/2000

OTHER PUBLICATIONS

C Ferrara et al., "Integrated GPR and Unilateral NMR Approach to Estimate Water Content in a Porous Material", Advanced Ground Penetrating Radar (IWAGPR), 2011 6th International Workshop on, IEEE, Jun. 22, 2011, pp. 1-4, ISBN 978-1-4577-0333-1 (electronic), 978-1-4577-0332-4 (print).

Pablo J. Prado, "NMR hand-held moisture sensor", Magnetic Resonance Imaging 19, Elsevier Science, 2001, pp. 505-508, ISSN 0730-725X.

Luca Senni et al., "Moisture content and strain relation in wood by Bragg grating sensor and unilateral NMR", Wood Science and Technology, Journal of the International Academy of Wood Science Springer, Berlin, DE, Jul. 15, 2009, pp. 165-175, XP019777953.

* cited by examiner

HAND-HELD MEASURING APPARATUS AND METHOD FOR THE OPERATION THEREOF

This application is a 35 U.S.C. § 371 National Stage Application of PCT/EP2015/068414, filed on Aug. 11, 2015, which claims the benefit of priority to Serial No. DE 10 2014 218 364.2, filed on Sep. 12, 2014 in Germany, the disclosures of which are incorporated herein by reference in their entirety.

BACKGROUND

The present disclosure relates to a mobile measuring appliance, in particular a hand-held measuring appliance, for nondestructive determination of a material measurement value relating to a material property of a workpiece.

DE 10 2008 055 196 A1 has disclosed an apparatus for transmitting and/or receiving electromagnetic radiofrequency signals, in particular an ultra-broadband sensor unit for a radar device comprising at least one planar emitter element. In particular, the apparatus may be used for detecting and classifying wall moisture.

SUMMARY

The mobile measuring appliance, in particular the handheld measuring appliance, according to the disclosure proceeds from a measuring appliance for nondestructive determination of a material measurement value relating to a material property of a workpiece, in particular a material measurement value in a workpiece, said measuring appliance comprising a housing, provided in which there is at least a first sensor apparatus, a second sensor apparatus, a control apparatus for actuating the first sensor apparatus and/or the second sensor apparatus, an evaluation apparatus for evaluating at least one measurement signal supplied by the first sensor apparatus and/or the second sensor apparatus, and an apparatus for supplying energy to the measuring appliance.

According to the disclosure, the first sensor apparatus comprises at least one nuclear magnetic resonance sensor (NMR sensor) and the second sensor apparatus comprises at least one sensor based on dielectric and/or resistive methods, wherein an information item about the material property of the workpiece, in particular moisture present in the workpiece, is obtained by evaluating a measurement signal supplied by the first sensor apparatus, said information item being provided for optimized actuation of the second sensor apparatus and/or optimized evaluation of measurement signals supplied by the second sensor apparatus.

Workpiece should, in particular, be understood to mean contiguous parts of a material. By way of example, and not exhaustively, the workpiece may be a wall, a floor, a ceiling, screed, an organic entity (in particular parts of a body) and/or parts of a terrain. By way of example, these materials may consist of, in particular, wood, glass, plastic, concrete, stone, brick, gypsum, metal, organic materials or the like. Further, in principle, it is also possible to examine liquids.

Below, "material measurement value relating to a material property of a workpiece" should be understood to mean, in particular, an item of information characterizing the material which is ascertained by using the measuring appliance. Preferably, the information item is a quantitative statement about a physical and/or chemical variable or property which, in particular, is describable by means of a characteristic and/or a numerical value. Alternatively or additionally, the material measurement values may also comprise a logic and/or comparative statement. By way of example, "material measurement values relating to a material property of the workpiece" may be understood to mean, in particular, values which relate to a density, a porosity, a concentration, in particular a concentration of a different type of material in the material of the workpiece, a mixture ratio of one or more materials, a composition of a material, etc. Particularly preferably, a material measurement value relating to the material property of the workpiece may also characterize moisture present in the workpiece.

In particular, hand-held measuring appliance should be understood to mean that the measuring appliance may be transported and, in particular, guided along a workpiece, even during a measurement process, without the aid of a transport machine merely using the hands, in particular using one hand. To this end, the mass of the hand-held measuring appliance is in particular less than 5 kg, advantageously less than 3 kg and particularly advantageously less than 1 kg. Preferably, the measuring appliance may have a handle or a handle region, by means of which the measuring appliance may be guided over an object to be examined, in particular guided over a workpiece.

It is proposed that the components of the sensor apparatuses, of the control apparatus, of the evaluation apparatus and of the apparatus for supplying energy to the measuring appliance are housed, at least in part, in the housing of the measuring appliance. In particular, in terms of the overall volume thereof, the components are housed in the housing of the measuring appliance to an extent of more than 50%, preferably to an extent of more than 75% and particularly preferably to an extent of 100%. It is thus possible to realize a compact measuring appliance which is easily guidable in one hand. Moreover, this allows the components to be advantageously protected from damage and ambient influences, for example moisture and dust.

The mobile measuring appliance comprises a control apparatus for actuating the first sensor apparatus and/or the second sensor apparatus. In particular, the control apparatus should be understood to mean an apparatus comprising at least one item of control electronics which comprises means for communicating with the other components of the measuring appliance, for example means for open-loop and closed-loop control of the first sensor apparatus and/or the second sensor apparatus, and/or means for data processing and/or further means appearing expedient to a person skilled in the art. In particular, the control apparatus is provided to set at least one operating functional parameter of the measuring appliance depending on at least one user input and/or an evaluation result of the evaluation unit. In particular, "provided" should be understood to mean, specifically, "programmed", "configured" and/or "equipped". An object being "provided" for a specific function should be understood to mean, in particular, that the object fulfills and/or carries out this specific function in at least one application and/or operating state, or it is configured to fulfill the function. Advantageously, the control electronics of the control apparatus according to the disclosure may be understood to mean a processor unit in conjunction with a memory unit and an operating program stored in the memory unit, said operating program being run during the control process. In particular, the electronic components of the control apparatus may be arranged on a circuit board (printed circuit board), preferably in the form of a microcontroller. Particularly advantageously, the control apparatus may moreover be provided to control the entire measuring appliance and facilitate the operation thereof. To this end, the control apparatus is provided to communicate with the other components of the measuring appliance, in particular with the first sensor apparatus and the second sensor apparatus, the evaluation apparatus, an input apparatus and/or an output apparatus, and also a data communication interface.

The evaluation apparatus for evaluating at least one measurement signal supplied by the first sensor apparatus and/or the second sensor apparatus should be understood to mean at least one apparatus which comprises an information input for receiving measurement signals, an information processing unit for processing, in particular evaluating, the received measurement signals, and an information output for forwarding the processed and/or evaluated measurement signals. Advantageously, the evaluation unit comprises components which comprise at least a processor, a memory and an operating program with evaluation and calculation routines. In particular, the electronic components of the evaluation apparatus may be arranged on a circuit board (printed circuit board), preferably on a common circuit board with the control apparatus, particularly preferably in the form of a microcontroller. Further, the control apparatus and the evaluation apparatus may particularly preferably also be embodied as a single component. The evaluation apparatus is provided to evaluate the measurement signals obtained by the first sensor apparatus and/or the second sensor apparatus and derive therefrom at least one information item relating to a material property of the workpiece, in particular relating to moisture present in the workpiece.

Further, the evaluation apparatus and/or the control apparatus may have stored correction tables and/or calibration tables, which render it possible to interpret and/or convert and/or interpolate and/or extrapolate evaluation results and calibrate the measuring appliance, in particular in respect of a workpiece material.

The apparatus for supplying the measuring appliance with energy is provided to supply the measuring appliance with electric energy for starting up purposes and during operation. Preferably, this apparatus is a power-grid-independent energy store, in particular an accumulator, a battery, a fuel cell, a capacitor, a different energy store appearing expedient to a person skilled in the art or a combination/plurality thereof. Preferably, accumulators with a cell chemistry providing a high power density and/or energy density are suitable, in particular, for supplying the measuring appliance with energy. By way of example, these currently include accumulators with lithium and lithium ion cell chemistry, in particular lithium iron phosphate accumulators, lithium manganese oxide accumulators, lithium nickel cobalt manganese oxide accumulators, over-lithiated lithium nickel cobalt manganese oxide accumulators, lithium sulfur accumulators, lithium polymer accumulators and lithium oxygen accumulators. Preferably, the apparatus for supplying energy has a detachable interlocking and/or force-fit connection interface. In this context, detachable should be understood to mean, in particular, separable in a nondestructive manner. Hence, the apparatus for supplying energy is arrangeable on the measuring appliance in a preferably removable and interchangeable manner. Particularly preferably, the removable apparatus for supplying energy may be resupplied and charged with energy from a power grid when within and/or outside of the measuring appliance.

According to the disclosure, the first sensor apparatus of the measuring appliance comprises at least one nuclear magnetic resonance sensor, which is provided at least to obtain a first information item about a material property of the workpiece, in particular about moisture present in the workpiece, in particular to determine a moisture measurement value of the workpiece, in particular to determine a moisture measurement value in the workpiece. The functionality of the nuclear magnetic resonance sensor is based on the nuclear physical effect in which atomic nuclei of a material sample, in particular in the workpiece, absorb and emit alternating electromagnetic fields in a magnetic field. Here, the nuclear magnetic resonance is based on the precession (Larmor precession) of nuclear spins of the atomic nuclei in the material sample about the magnetic field lines of a constant, in particular static, first magnetic field. In particular, the nuclear spins of the atomic nuclei in the material sample are aligned by the first magnetic field. If energy is radiated in onto the atomic nuclei in the form of a second electromagnetic field, in particular an alternating field, for example a pulsed magnetic field, said energy being resonant with the Larmor precession of the nuclear spins of said atomic nuclei (energy quanta), the atomic nuclei may change the orientation of the spins thereof relative to the first magnetic field by absorbing this energy. The second radiated-in magnetic field therefore serves to excite the nuclear spins which change their nuclear spin states under the uptake of energy. Equivalently, the emission of energy quanta as a consequence of a return of the excited nuclear spins into a different, lower energy level leads to the emission of an alternating electromagnetic field which may be observed by means of an apparatus for detecting a magnetic field change, in particular an antenna and/or a coil.

Advantageously, the nuclear magnetic resonance sensor allows the excitation of atomic nuclei of the material sample in the workpiece by means of alternating electromagnetic fields and the generation of an output signal on the basis of a nuclear magnetic resonance effect. In the case of a suitable selection of the operating parameters of the nuclear magnetic resonance sensor, it is directly possible to deduce the quantity of an element species, in particular the quantity of hydrogen atoms, in the examined volume by way of the amplitude and/or relaxation times of the response signal, from which it is possible to evaluate an information item about the material property of the workpiece, in particular an information item about moisture present in the workpiece. Advantageously, absolute moisture measurement values of the material of the workpiece, in particular, may be determined thus.

In particular, excitation of atomic nuclei should be understood to mean that the energy of the radiated-in electromagnetic fields, in particular alternating fields, brings about a change in the nuclear spins of the atomic nuclei. Furthermore, the assumption is made below that, in particular, changeable magnetic fields are coupled to electric fields (cf. Maxwell's equations), and so no distinction is made between an electric field and a magnetic field. In particular, the energy transferred by radiated-in electromagnetic radiation matters for exciting nuclear magnetic resonance effects. Advantageously, this energy may be transferred by means of pulsed electromagnetic fields.

As described above, "material property of a workpiece" should, in particular, be understood to mean a property at least partly characterizing the material which is ascertained by using the measuring appliance. Preferably, here, this is a physical property and/or a chemical property of the material of the workpiece and/or of other materials included in the workpiece. Below, examples relating to an examination of moisture in the workpiece are mainly presented for elucidating the advantages of the disclosure. Naturally, the relevant principles may also be transferred to other material properties, in particular e.g. densities, porosities, concentrations, in particular concentrations of a different type of material in the material of the workpiece, mixture ratios of one or more materials, compositions of the material, etc. Within this meaning, the term moisture used below may also be replaced by any other term describing the material property of a workpiece and, in particular, also by the aforementioned terms such as density, porosity, concentration, mixture ratio, composition and the like.

Determining a moisture measurement value of a workpiece, in particular in a workpiece, by means of the nuclear magnetic resonance sensor should be understood to mean, in particular, deriving statements from the obtained nuclear magnetic resonance measurement data, said statements, inter alia, relating to a relative and/or absolute moisture content and/or a moisture gradient into the workpiece and/or binding states of the water forming the moisture and/or time-dynamic processes of the water forming the moisture. Particularly advantageously, the mobile measuring appliance permits the determination of moisture measurement values of a workpiece, in particular in a workpiece, without destroying the workpiece. In particular, the measurement method is a nondestructive, in particular contactless measurement method, i.e., in one embodiment of the measuring appliance according to the disclosure, a moisture measurement value may also be obtained without any contact between the measuring appliance and the sample to be measured, optionally also without contact with the workpiece to be examined. Positioning the measuring appliance, in particular the nuclear magnetic resonance sensor contained therein, in the direct vicinity of the workpiece surface facilitates the determination of moisture measurement values into the workpiece down to a material depth of a few centimeters. Particularly advantageously, the nuclear magnetic resonance sensor thus permits absolute determination of a moisture profile, in particular a gradient of the moisture in the material of the workpiece, down to this material depth in an accessible measurement region. In particular, the realizable measurement depth is limited by physical parameters of the nuclear magnetic resonance sensor.

For the purposes of determining material measurement values relating to the material property of a workpiece, in particular moisture measurement values, provision may be made for a calibration of the measuring appliance, in particular a calibration of the sensor apparatus. In relation to the example of determining the moisture, it is possible, for example, to carry out a calibration measurement on a pure water sample (e.g. a glass filled with water), which is carried out after switching on the measuring appliance, for the purposes of stipulating a maximum moisture (corresponding to 100%) and hence of calibrating the measuring appliance. All subsequent measurements, in particular measurements on a workpiece to be examined, are subsequently evaluated in relation to this calibration measurement. Should the volume examined by means of the sensor apparatus be known, it is furthermore possible to evaluate absolute moisture and volumetric variables, in particular a concentration, a volume percentage information item or the like.

Moreover, it is advantageously possible to ascertain further information items, for example relating to the composition, layer thicknesses and/or salt content of the material of the workpiece.

Furthermore, according to the disclosure, the measuring appliance comprises a second sensor apparatus which comprises at least one sensor based on dielectric and/or resistive methods. Advantageously, this second sensor apparatus permits a nondestructive determination of a second information item relating to the material property of the workpiece, in particular the moisture of the workpiece, by means of emitting and/or receiving and/or measuring electromagnetic fields penetrating into the workpiece, in particular also emitting and/or receiving and/or measuring radiofrequency signals penetrating into the workpiece.

This second sensor apparatus renders it possible to ascertain further information items, not necessarily redundant information items, in addition to the information items determined by the first sensor apparatus. According to the disclosure, it is possible to obtain complementary information items, i.e. information items relating to different material properties of the workpiece, and/or information items relating to the same material property of the workpiece using both sensor apparatuses.

According to the disclosure, it is proposed that an information item about a material property of the workpiece, in particular moisture present in the workpiece, is obtained by evaluating at least one measurement signal supplied by the first sensor apparatus, said information item being provided for optimized actuation of the second sensor apparatus and/or optimized evaluation of the measurement signals supplied by the second sensor apparatus. Hence, it is particularly advantageously possible to use a measurement result obtained using the nuclear magnetic resonance sensor, i.e., in particular, an absolute moisture measurement value and/or a moisture gradient within the measurement region (measurement depth) of the nuclear magnetic resonance sensor, for optimized actuation of the second sensor apparatus and/or optimized evaluation of measurement signals supplied by the second sensor apparatus.

In particular, "optimized actuation of the second sensor apparatus" should be understood to mean that the first information item relating to the material property of a workpiece is used to influence, advantageously improve and/or optimize, particularly advantageously calibrate, at least a characteristic and/or a control parameter of the control apparatus for actuating the second sensor apparatus with the goal of carrying out measurements with the second sensor apparatus which are adapted to the conditions of the workpiece and hence are improved and/or more accurate. In an advantageous and non-exhaustive fashion, these control parameters and characteristics may relate to physical and/or technical parameters such as e.g. voltages, currents, pulse durations, powers, emission directions, etc., for operating the second sensor apparatus.

In particular, "optimized evaluation of measurement signals supplied by the second sensor apparatus" should be understood to mean that the first information item relating to the material property of the workpiece is used to influence, advantageously improve and/or optimize, particularly advantageously calibrate, at least an evaluation routine and/or an evaluation process of the evaluation apparatus with the goal of facilitating evaluations of measurement signals supplied by the second sensor apparatus which are adapted to the conditions of the workpiece and hence are improved and/or more accurate. Particularly advantageously, the optimized evaluation facilitates relating information items relating to the material property, in particular the moisture, which are ascertained by the second sensor apparatus, in particular e.g. relative moisture measurement values, to an information item relating to the material property of the workpiece, in particular the moisture of the workpiece, which is ascertained by the first sensor apparatus, in particular e.g. to an absolute moisture measurement value and/or a moisture gradient into the workpiece. It is thus possible to carry out a calibration of measurement signals from the second sensor apparatus and/or a calibration of the evaluation of these measurement signals in a particularly advantageous manner.

In an advantageous embodiment of the measuring appliance according to the disclosure, the second sensor apparatus comprises at least one sensor from a group of capacitance sensors, microwave sensors, ultrasonic sensors, resistance sensors, conductivity sensors and/or radar sensors, in particular ultra-broadband radar sensors and/or broadband impulse radar sensors.

In relation to the example of moisture, a surface-near determination of a moisture measurement value, in particular a relative moisture measurement value, may be carried out on the basis of resistive measurement methods, for example by means of a conductivity measurement between two tips pressed into the workpiece. Alternatively and/or additionally, it is possible, for example, to obtain a permittivity of the surface-near material of the workpiece by electrodes placed on the workpiece on the basis of capacitive measurement methods.

Advantageously, the use of radar waves and/or microwaves which are radiated into the workpiece by means of at least one antenna and the material-internal reflections and/or scattering of which are received facilitates ascertaining material measurement values relating to a material property of a workpiece at a significantly larger measurement depth, particularly in comparison with the nuclear magnetic resonance measurement method or the conductivity measurement method.

Advantageously, the use of radar waves and/or microwaves therefore also facilitates ascertaining the permittivity of the workpiece at a significantly larger measurement depth, particularly in comparison with the nuclear magnetic resonance measurement method or the conductivity measurement method. This measurement method likewise allows an uncalibrated, in particular relative measurement of a moisture measurement value of the workpiece, in particular in the workpiece. In particular, it is possible to realize relative moisture measurements for material depths of down to 10 cm, advantageously of down to 15 cm and particularly advantageously of greater than 15 cm.

A radar sensor may particularly advantageously be used for depth-resolved measurement.

In particular, an absolute moisture measurement in this measurement method is only possible if the dry permittivity $\varepsilon_T$, i.e. the permittivity of the completely dry material of the workpiece, is known and hence the measured moisture measurement value may be related to the dry permittivity $\varepsilon_T$ and a corresponding mass component of water may be calculated.

Particularly advantageously, a measurement result obtained using the nuclear magnetic resonance sensor, i.e., in particular, an absolute moisture measurement value and/or a moisture gradient within the measurement region (measurement depth) of the nuclear magnetic resonance sensor, may be used for optimized actuation of the second sensor apparatus and/or optimized evaluation of measurement signals supplied by the second sensor apparatus.

A moisture measurement value ascertained by the nuclear magnetic resonance sensor, in particular an absolute moisture measurement value and/or a moisture gradient into the workpiece, may contribute to determining the dry permittivity $\varepsilon_T$ of the material of the workpiece and hence be used as calculation basis for the second sensor apparatus, for example a radar sensor. In particular, provision may be made for determining the dry permittivity $\varepsilon_T$ from only measurement signals of the nuclear magnetic resonance sensor or with the aid of measurement signals from the second sensor. In this way, it is particularly advantageously possible to ascertain absolute moisture measurement values down to a significantly larger material depth into the workpiece and the measurement region of the measuring appliance may be significantly increased. In this way, it is possible, in particular, to realize absolute moisture measurements for material depths of down to 10 cm, advantageously of down to 15 cm and particularly advantageously of greater than 15 cm.

In an advantageous embodiment of the mobile measuring appliance, the nuclear magnetic resonance sensor of the mobile measuring appliance comprises a first apparatus for generating a first magnetic field, in particular a first magnetic field with a defined field gradient, a second apparatus, in particular a radiofrequency coil and/or an antenna, for generating a second magnetic field, the latter superimposing the first magnetic field, wherein the control apparatus comprises at least one control unit for controlling the second apparatus, wherein the control unit is provided, in particular, for modifying the second magnetic field, in particular for generating pulse sequences.

The first magnetic field generated by the first apparatus serves to align the nuclear spins of the atomic nuclei present in the material of the workpiece in the sense that the nuclear spins align along the magnetic field lines of the magnetic field on account of the nuclear spin magnetic moment thereof, in particular precess about the magnetic field lines of the magnetic field. The nuclear spins are excited as a consequence of radiating in energy in the form of an electromagnetic field generated by means of the second apparatus, in particular an alternating electromagnetic field, for example a pulsed magnetic field.

The first apparatus for generating a first magnetic field, in particular with a defined field gradient, may be understood to mean, in particular, apparatuses such as permanent magnets, electromagnets, coil apparatuses. The magnetic field generated by the first apparatus is typically denoted $B_0$.

In principle, the second apparatus for generating a second magnetic field may be understood to mean the same means; however, this second apparatus is advantageously realized by means of a radiofrequency coil and/or an antenna. The radiofrequency coil is particularly advantageously operated at a frequency in the megahertz range. In particular, the frequency lies below 900 megahertz, preferably below 200 megahertz and particularly preferably below 50 megahertz.

The control unit for controlling the second apparatus, i.e. for controlling preferably the radiofrequency coil, facilitates generating pulse sequences of the second magnetic field such that the second magnetic field generated by the second apparatus may be modified in a temporal and spatially dependent manner. By means of the pulse sequences, it is particularly advantageously possible to excite the nuclear spins of the atomic nuclei of the material present in the examined workpiece to absorb and emit energy quanta, in particular to become resonant, by means of alternating electromagnetic fields.

In an advantageous embodiment of the measuring appliance according to the disclosure, the nuclear magnetic resonance sensor comprises an apparatus for detecting a magnetic field change, in particular a reception coil for detecting a magnetic field change, said apparatus facilitating the deduction of material-specific characteristics by means of magnetic field changes caused by nuclear spin relaxation.

Advantageously, the device for detecting a magnetic field change can be used to detect a nuclear magnetic resonance effect of the excited nuclear spins of the atomic nuclei, which are present in the workpiece, as a consequence of influencing the first magnetic field and/or the second magnetic field. Flipping of the nuclear spins of the atomic nuclei, during which an electromagnetic field is emitted, may particularly advantageously be detected in the form of a voltage induced by the magnetic field variation and/or an induced current by means of a reception coil. This voltage and/or this current may be forwarded to the evaluation apparatus for evaluating the nuclear spin signal.

In an alternative embodiment of the measuring appliance according to the disclosure, the reception coil may also be realized by the radiofrequency coil of the second apparatus for generating the second magnetic field. In this case, the resonance of the nuclear spins of the atomic nuclei becomes observable by virtue of flipping of the nuclear spins, followed by an emission of an electromagnetic field, inducing a voltage (equivalently: a current) in the coil which is superimposed on the applied AC voltage such that influences on the power required to operate the radiofrequency coil may be detected.

In an advantageous embodiment of the measuring appliance according to the disclosure, the first magnetic field generated by the first apparatus of the nuclear magnetic resonance sensor is aligned substantially parallel to a first housing side of the measuring appliance and the magnetic field generated by the second apparatus is aligned substantially perpendicular to the first magnetic field.

The first housing side is a substantially planar outer wall of the housing which delimits the measuring appliance from the surroundings thereof. In particular, when using the measuring appliance, the first housing side faces the workpiece to be examined and, in particular, faces away from a user.

The orientation of the first magnetic field may be generated by at least two permanent magnetic poles (north, south) of a permanent magnet, particularly if the poles are situated in a north-south alignment parallel to, and in the vicinity of, the first housing side. This arrangement may be realized by using a horseshoe magnet in a particularly structurally simple manner.

The first magnetic field used to align the nuclear spins of the atomic nuclei present in the material sample has, in particular, a magnetic field strength of more than 0.1 tesla, preferably of more than 1.5 tesla and particularly preferably of more than 5 tesla. In particular, strong permanent magnets suitable for generating this magnetic field are, for example, produced from ferrites or, preferably, as an iron cobalt nickel alloy or, particularly preferably, as a neodymium iron boron alloy or a samarium cobalt alloy.

Alternatively, the magnetic field alignment of the first magnetic field may be realized by at least two permanent magnets which are aligned in antiparallel fashion perpendicular to the surface of the first housing side of the measuring appliance, in particular within the housing, and aligned in the vicinity of the first housing side. The magnetic field lines extending from the north pole of the first permanent magnet to the south pole of the second permanent magnet may be considered to be substantially parallel to the first housing surface of the measuring appliance if the two permanent magnets are aligned at a distance from one another. In particular, "substantially parallel" should be understood to mean that a first region exists, in which the magnetic field lines describing the first magnetic field may be considered to be virtually parallel. In particular, the deviation of the magnetic field lines from a theoretical parallel in this first region is less than 20 degrees, advantageously less than 10 degrees and particularly advantageously less than 5 degrees.

The second magnetic field which extends substantially perpendicular to the first magnetic field may be generated by a coil and/or an antenna, in particular by a radiofrequency coil, in a particularly advantageous embodiment. To this end, the coil is, in particular, arranged in a plane parallel to, and in the immediate vicinity of, the surface of the first housing side, preferably in the interior of the housing, but alternatively outside on the housing or in the housing wall as well. The magnetic field lines of the magnetic field generated by the coils with the current flowing therethrough extend perpendicular to the plane of the coil in the vicinity of the coil. Here, "substantially perpendicular to the first magnetic field" should be understood to mean that a second region exists, in which the magnetic field lines describing the second magnetic field may be considered to be virtually perpendicular to the magnetic field lines of the first magnetic field. In particular, the angular deviation of the magnetic field lines of the first magnetic field and of the second magnetic field from the perpendicular is less than 20 degrees, advantageously less than 10 degrees and particularly advantageously less than 5 degrees. The first region and the second region particularly advantageously coincide.

The magnetic field alignment of the first magnetic field may likewise be achieved by two permanent magnets arranged parallel to the first housing side and collinearly, i.e. in a north-south/north-south sequence, with a radiofrequency coil being situated between these two permanent magnets, the winding plane of said radiofrequency coil lying collinearly with the direction of extent of the permanent magnets and parallel to the first housing side. Here, the described arrangement is likewise positioned in the vicinity of the first housing side.

What is advantageously achieved by suitably positioning the apparatuses for generating the magnetic fields in the vicinity of the first housing side is that the region in which the two magnetic fields are superimposed is at least partly situated outside of the housing of the measuring appliance, and so an intrusion of the magnetic fields into the workpiece to be examined is facilitated.

In an alternative embodiment, the first magnetic field generated by the first apparatus of the nuclear magnetic resonance sensor is aligned substantially perpendicular to the first housing side of the measuring appliance and the second magnetic field generated by the second apparatus is aligned substantially perpendicular to the first magnetic field.

In an advantageous embodiment of the mobile measuring appliance, the second apparatus of the nuclear magnetic resonance sensor for generating the second magnetic field, in particular the radiofrequency coil, is realized in an interchangeable manner.

In particular, "interchangeable" should be understood to mean that the radiofrequency coil has a detachable interlocking and/or force-fit connection interface, by means of which the coil is separable from the measuring appliance in a nondestructive manner, in particular interchangeable by an end-user. Hence, the coil is arrangeable on the measuring appliance in a preferably removable and interchangeable manner. For the purposes of realizing the interchangeable property, the measuring appliance may have an access to the second apparatus of the nuclear magnetic resonance sensor, in particular on the first housing side.

What may be realized thus is that coils with different characteristics, in particular winding numbers, geometries and wire thicknesses, may be changed in a nondestructive manner and subsequently used. Advantageously, the magnetic fields generated by the second apparatus may be varied and adapted to the required operating conditions, in particular the material of the workpiece to be examined, by way of a suitable selection of the coil. Further, what may be achieved is that the region in which the first magnetic field and the second magnetic field superpose is shifted in terms of the position thereof and/or modified in terms of the geometry thereof.

In an advantageous embodiment of the mobile measuring appliance, the magnetic fields of the nuclear magnetic resonance sensor define a first sensitive region of the nuclear magnetic resonance sensor, in particular a layer-shaped region which extends substantially parallel to and at a distance from the first housing side outside of the housing of the measuring appliance.

In particular, this first sensitive region lies in the superposition field of the first magnetic field and the second magnetic field. Depending on the frequency (Larmor frequency) of the radiated-in electromagnetic field and the static magnetic field strength of the first magnetic field, the first sensitive region is, in an ideal case, defined by an area in which the magnetic field strength of the first magnetic field is constant and, in particular, has a defined magnitude. In reality, this area is, in fact, layer-shaped on account of non-exact, i.e. non-discrete, frequencies. Since, furthermore, the magnetic field lines do not extend exactly parallel to one another, the first sensitive region may consequently be curved along the magnetic field lines and/or inhomogeneous, in particular inhomogeneous in respect of the layer extent thereof.

What may be achieved in a particularly advantageous manner thus is that the magnetic fields penetrate into the workpiece and the first sensitive region of the nuclear magnetic resonance sensor comes to rest in the workpiece by means of positioning the mobile measuring appliance on a workpiece surface, with the first housing side of the measuring appliance being positioned in the immediate vicinity of the surface of the workpiece to be examined.

In an alternative and/or additional embodiment of the measuring appliance, the sensor apparatus may be operated in such a way that the sensitive region in the superposition field of the two magnetic fields is situated within the housing, in particular in the interior of the nuclear magnetic resonance sensor, preferably centrally between the two permanent magnet poles spanning the first magnetic field. In this manner, it is possible to realize a measuring appliance in a structurally simple manner, with material samples being able to be introduced into said measuring appliance for measurement purposes. By way of example, this allows material samples to be introduced into the measuring appliance through an opening in the first housing side of the measuring appliance by means of a sample tube in such a way that said material samples come to rest centrally between the two permanent magnet poles spanning the first magnetic field and hence in the sensitive region of the nuclear magnetic resonance sensor. Particularly advantageously, provision may be made for switchover between the different arrangements of the sensitive region, in particular between a positioning of the sensitive region within and outside of the housing of the measuring appliance, to be possible. Such a switchover may advantageously be realized mechanically (for example by shielding and/or repositioning of the first apparatus and/or the second apparatus for generating the first magnetic field or the second magnetic field in the measuring appliance) or electronically (for example by modifying the frequency in the radiofrequency coil).

If the volume defined by the first sensitive region, i.e. the volume of the material of the workpiece which is examined during a measurement, is known, it is possible to evaluate absolute values and, in particular, also volumetric variables of the material measurement value relating to the material property, in particular the moisture measurement value, for example a concentration, a volume percentage information item or the like. The volume defined by the first sensitive region may advantageously be known for structural reasons and/or as a result of a measurement using apparatuses.

It is furthermore proposed that the first sensitive region of the nuclear magnetic resonance sensor may be displaced, in particular displaced mechanically and/or electronically, advantageously by 1 cm, particularly advantageously by 2 cm, in particular by 3 cm, outside of the housing along a perpendicular to the first housing side of the measuring appliance.

Here, the displacement of the first sensitive region may advantageously be achieved by a modification of the magnetic fields, for example by a change in the geometry and/or homogeneity thereof by means of a coil (a so-called shim coil) or by means of (displaceable) magnetic shielding, particularly advantageously also by a change in the frequency of the radiofrequency coil, and by a mechanical displacement of the nuclear magnetic resonance sensor in the housing of the measuring appliance. Consequently, the first sensitive region may be displaced within the workpiece in the case of constant positioning of the measuring appliance in such a way that a depth-resolved measurement, for example a measurement of a depth profile and/or a gradient of the moisture measurement value into the workpiece, may be realized in a simple and particularly economical manner.

In an advantageous embodiment of the measuring appliance according to the disclosure, the second sensor apparatus has a second sensitive region which extends substantially symmetrically in relation to the perpendicular in relation to the first housing side of the measuring appliance along said perpendicular.

In particular, "second sensitive region" should be understood to mean a direction of extent, a solid angle or a spatial volume in which the second sensor apparatus has a maximum sensitivity. By way of example, in the case of a radar sensor this direction of extent represents the chief emission direction (solid angle) of the electromagnetic radiation. In the case of a sensor apparatus provided to have a maximum sensitivity at different solid angles in different operating states, "second sensitive region" should advantageously be understood to mean the respective solid angle or a mean solid angle.

What may advantageously be achieved therefore is that the first sensor apparatus and the second sensor apparatus of the measuring appliance have, in particular, identical chief measuring directions which lie substantially parallel to the perpendicular in relation to the first housing side. In particular, the "chief measuring direction" should then be understood to mean a straight line along which the first sensitive region of the first sensor apparatus may be displaced and along which the second sensitive region of the second sensor apparatus substantially extends. Hence, what may be achieved according to the disclosure is that the conditions of the material in the workpiece which underlie the measurements of the material property, in particular the moisture, by means of the first sensor apparatus and the second sensor apparatus are similar, in particular identical, for the measurement with the first sensor apparatus and with the second sensor apparatus. The volumes of the workpiece defined by the sensitive regions overlap.

In an alternative embodiment of the measuring appliance according to the disclosure, the second sensor apparatus has an alternative second sensitive region which extends substantially along a straight line parallel to the perpendicular in relation to the first housing side of the measuring appliance.

In this embodiment, the volumes of the workpiece defined by the sensitive regions of the first sensor apparatus and of the second sensor apparatus do not necessarily overlap.

In an advantageous embodiment of the measuring appliance according to the disclosure, provision is made of means which allow the direction of extent and/or the homogeneity and/or the geometry of the first sensitive region and/or of the second sensitive region to be influenced.

In particular, these means may, for example, be understood to mean electrodes and/or coils (so-called shim coils) which generate electromagnetic fields, with the aid of which correction and/or superposition fields are generated, rendering it possible to influence, in particular homogenize, the direction of extent and/or the homogeneity and/or the geometry of the first sensitive region and/or of the second sensitive region to a desired, advantageous extent.

Homogenization of a sensitive region should be understood to mean, in particular, that the field lines describing the electromagnetic field and the local electric field strength or magnetic field strength thereof are subject to only small variations, ideally no variations, and, in particular, do not have any field distortions.

Furthermore, geometric deformations of the sensitive regions, for example a reduction or enlargement corresponding to focusing or defocusing of the sensitive region, may be achieved by these means.

Furthermore, it is proposed that provision is made of shielding means which allow mutual interference influences among the sensor apparatuses to be minimized.

This electromagnetic shielding, which may, in particular, consist of ferromagnetic materials and/or mu metal and/or electrically conductive elements, allows the course of the field lines of the electromagnetic fields of the first sensor apparatus and/or of the second sensor apparatus to be influenced and may advantageously be used to realize effective shielding of the sensor apparatuses from one another. Particularly advantageously, magnetic shielding may be used to shield the magnetic fields used by the nuclear magnetic resonance sensor, at least in part, from other interference influences, such as, in particular, electromagnetic radiation from the second sensor apparatus. This also applies vice versa. Further, components of the mobile measuring appliance may advantageously be shielded, at least in part, from electromagnetic radiation from the measuring-appliance-internal sensor apparatuses.

Mu metal (also: μ-metal) should be understood to mean a soft magnetic alloy with a high magnetic permeability which is usable for shielding magnetic fields.

Furthermore, such shielding means may likewise be counted as part of the means allowing the direction of extent and/or the homogeneity and/or the geometry of the first sensitive region and/or of the second sensitive region to be influenced.

It is proposed that, in an advantageous embodiment of the mobile measuring appliance, the evaluation apparatus is embodied to evaluate measurement signals supplied by the first sensor apparatus and/or the second sensor apparatus, in particular to evaluate a relative and/or absolute moisture content and/or a moisture gradient into the workpiece and/or binding states of the water forming the moisture and/or time-dynamic processes of the water forming the moisture and/or further structurally relevant parameters, in particular salt content, composition, density, inhomogeneity and porosity, of the material of the workpiece.

Particularly advantageously, the evaluation apparatus for evaluating measurement signals supplied by the first sensor apparatus is embodied to evaluate at least a relative and/or absolute moisture content and/or a moisture gradient into the workpiece and/or binding states of the water forming the moisture and/or time-dynamic processes of the water forming the moisture and/or further structurally relevant parameters, in particular salt content, composition and/or porosity, of the material of the workpiece by determining the number of 1H atoms in the workpiece.

Hence, according to the disclosure, the mobile measuring appliance may be used to comprehensively characterize a workpiece in respect of moisture in a surface-near region corresponding to the measurement depth by means of the nuclear magnetic resonance sensor. Statements about the relative and/or absolute moisture content and about a moisture gradient into the workpiece facilitate a reliable evaluation of the workpiece, in particular in respect of processability, dryness, risk of damp, strength, resilience and the like. In particular, an information item obtained about the moisture of the workpiece may be used for determining the dry permittivity $\varepsilon_T$ of the material of the workpiece. This information item relating to the dry permittivity $\varepsilon_T$ may be used, according to the disclosure, for the optimized actuation of the second sensor apparatus and/or optimized evaluation of measurement signals supplied by the second sensor apparatus.

Statements relating to the binding states of the water forming the moisture moreover permit determination as to whether the moisture is free water, capillary water, physisorbed or chemisorbed water, crystallization water, etc. Further conclusions relating to a possible drying behavior and/or drying result may be derived therefrom.

By recording and evaluating time-dynamic processes of the water forming the moisture, it is possible to examine processes such as migration, convection and travel of water, in particular of waterfronts, in the material. Conclusions relating to a possible drying or drenching behavior and/or a drying result may be derived therefrom.

Further structurally relevant parameters which may be evaluated by the evaluation apparatus of the mobile measuring appliance using measurement signals supplied by the nuclear magnetic resonance sensor comprise, in particular, salt content, composition and/or mixing ratio of the material of the workpiece and the density and/or porosity thereof, but also further parameters appearing expedient to a person skilled in the art.

Further, the evaluation apparatus for evaluating measurement signals supplied by the second sensor apparatus is particularly advantageously embodied, in particular, to evaluate a relative moisture measurement value of the material of the workpiece, in particular evaluate the latter with depth resolution.

According to the disclosure, this facilitates ascertaining the permittivity of the workpiece at a significantly larger measurement depth, particularly when compared with the nuclear magnetic resonance measurement method, using electromagnetic fields which penetrate deep into the workpiece, for example when using radar waves and/or microwaves.

Particularly advantageously, a measurement result obtained using the nuclear magnetic resonance sensor, i.e., in particular, an absolute moisture measurement value and/or a moisture gradient within the measurement region of the nuclear magnetic resonance sensor, may be used for optimized actuation of the second sensor apparatus and/or optimized evaluation of measurement signals supplied by the second sensor apparatus.

Furthermore, it is proposed that the control apparatus of the measuring appliance has an operating mode in which specifications relating to a workpiece may be specified by user inputs and/or may be made available to the measuring appliance.

In particular, an operating mode should denote information processing, an information output or an information input, in conjunction with which the control apparatus applies an operating program, a closed-loop control routine, an open-loop control routine, an evaluation routine and/or a calculation routine.

By way of example, specifications relating to a workpiece may relate to the material of the workpiece, the physical or chemical properties thereof or any other specifications appearing expedient to a person skilled in the art.

What is proposed for an advantageous embodiment is that the control apparatus of the measuring appliance has an operating mode in which output parameters of the output apparatus may be specified and/or may be made available to the measuring appliance.

Output parameters should be understood to mean all specifications relating to the output, in particular characteristics of interest to the user, output forms (e.g. as a number, a graphic, a map, converted equivalent variables), conversion options, error indications, correction factors, etc.

In an advantageous embodiment of the measuring appliance according to the disclosure, an input apparatus for inputting working parameters is present, in particular an input apparatus which is arranged in a second housing side of the measuring appliance.

In particular, an input apparatus should be understood to mean means provided to accept at least one information item from an operator of the measuring appliance, for example in the form of a user interface, and/or a different appliance by way of an acoustic, optical, gesture-assisted and/or tactile input and forward said input to the control apparatus of the measuring appliance. By way of example, the input apparatus may consist of an actuation element, a keyboard, a display, in particular a touch display, a voice input module, a gesture identification unit and/or a pointer appliance (e.g. a mouse). Further, the input apparatus may additionally also be present outside of the measuring appliance, for example in the form of an external data appliance such as a smartphone, a tablet PC, a PC, or in the form of another external data appliance appearing expedient to a person skilled in the art, said external data appliance being connected to the control apparatus of the measuring appliance by way of a data communication interface. The latter is advantageous, in particular, if the external data appliance permits and/or assists an expanded functionality of the measuring appliance, for example the creation of a multidimensional map or a floorplan with moisture measurement values.

Working parameters denote all necessary and/or expedient operating parameters of the measuring appliance, in particular for the control thereof, and parameters relating to the evaluation of the measurement results.

Housing side refers, in particular, to an outer wall of the housing delimiting the measuring appliance from the surroundings thereof. "Arranged in a housing side" should be understood to mean that, on the second housing side, the input apparatus and/or the output apparatus are/is introduced, applied or fastened by other means into the surface thereof. In particular, the housing itself may also be a constituent of the input apparatus or output apparatus.

Advantageously, the second housing side faces the operator when using the measuring appliance.

In an advantageous embodiment of the mobile measuring appliance, an output apparatus for outputting working parameters and/or evaluation results is present, in particular an output apparatus which is arranged in a second housing side of the measuring appliance.

An output apparatus should be understood to mean at least one means provided to output at least one varying information item to an operator in an acoustic, optical and/or tactile manner. By way of example, this may be realized by means of a display, a touch display, a sound signal, a change in an operating parameter, a vibration transducer and/or an LED display. In particular, information items to be output, for example evaluation results and/or information items relating to an operating state of the measuring appliance, may also be output to a machine controller, in particular also the control apparatus of the sensor apparatus, and/or, in particular for increasing the user convenience, to a data-processing system. The latter comprises at least one output of an information item to an external appliance such as a smartphone, a tablet PC, a PC and to any other external data appliance appearing expedient to a person skilled in the art, said external data appliance being connected to the evaluation apparatus of the measuring appliance by way of a data communication interface.

Hence, it is possible to advantageously house both the input apparatus and the output apparatus directly in the housing of the mobile measuring appliance and/or these may be outsourced and, for example, realized by way of external apparatuses. The latter realization option explicitly comprises the control, evaluation and output of the measurement results by way of wired and/or wireless external systems such as e.g. remote controls, computer controllers, tablet PCs and/or other mobile appliances such as cellular telephones, smartphones, etc.

In a particularly advantageous embodiment of the mobile measuring appliance according to the disclosure, the second housing side receiving the input apparatus and/or the output apparatus lies opposite the first housing side of the measuring appliance and, in particular, is arranged on the appliance rear side.

What may advantageously be achieved thus is that when the measuring appliance is positioned with the sensitive regions facing a workpiece, in particular when the first housing side is adjacent to the workpiece, said measuring appliance may be operated by way of the input and/or output apparatuses received on the second housing side of the measuring appliance and measurement results may be read.

In a further advantageous embodiment of the mobile measuring appliance according to the disclosure, provision is made of a position determination apparatus for capturing at least a current position and/or alignment of the measuring appliance, in particular in relation to the workpiece.

To this end, in particular, the position determination apparatus may comprise one or more sensors of a group of sensors comprising at least inclination sensors, angle sensors, distance sensors, translation sensors, acceleration sensors and rotational-rate-sensitive sensors. Moreover, determining the position may also be realized with other means appearing expedient to a person skilled in the art.

By way of example, the position determination apparatus may be realized using roller bodies, in particular using wheels arranged on the housing of the measuring appliance, said roller bodies recording the change in position when displacing the measuring appliance in relation to the workpiece. Since the distance between measuring appliance and workpiece should preferably be minimized for the purposes of increasing the penetration depth of the magnetic fields into the workpiece, the position determination apparatus may particularly preferably also be provided as an optical displacement transducer which is arranged in the housing side facing the workpiece to be examined when the measuring appliance is used.

It is furthermore proposed that the evaluation apparatus for evaluating measurement signals supplied by the first sensor apparatus and/or the second sensor apparatus is embodied to evaluate measurement signals from the first sensor apparatus and/or the second sensor apparatus depending on the position and/or alignment of the measuring appliance, in particular in relation to the workpiece.

What this may advantageously achieve is that evaluated parameters may be correlated with a position of the measuring appliance on the workpiece. Furthermore, successive measurement of a workpiece allows multidimensional matrices or maps, which capture measurement results in relation to positions and/or alignments of the measuring appliance, in particular in relation to the workpiece, to be created and/or evaluated. Particularly advantageously, this may be used to generate a representation of the evaluated measurement signals in the form of a map of the workpiece, in particular a multidimensional map as well.

At least one memory apparatus for storing measurement results and/or working parameters is provided in a further advantageous embodiment of the mobile measuring appliance.

This memory apparatus may comprise all forms of external and internal electronic, in particular digital, memories, in particular also memory chips such as USB sticks, memory sticks, memory cards, etc.

Moreover, it is proposed that the control apparatus and/or the evaluation apparatus of the measuring appliance according to the disclosure comprises a data communication interface for communication, in particular wireless communication, by means of which data communication interface the measuring appliance may transmit and/or receive measurement results and/or working parameters.

Preferably, the data communication interface uses a standardized communication protocol for transferring electronic data, in particular digital data. Advantageously, the data communication interface comprises a wireless interface, in particular e.g. a WLAN interface, Bluetooth interface, infrared interface, NFC interface, RFID interface, or any other wireless interface appearing expedient to a person skilled in the art. Alternatively, the data communication interface may also comprise a wired adapter, for example a USB adapter or micro-USB adapter.

Advantageously, measurement results and/or working parameters may, by way of the data communication interface, be transmitted from the measuring appliance to an external data appliance, for example to a smartphone, a tablet PC, a PC, a printer or further external appliances appearing expedient to a person skilled in the art, or said measurement results and/or working parameters may be received by the latter. Advantageously, a transfer of data which is usable for further evaluation of measurement signals captured by the measuring appliance may be facilitated by means of the configuration according to the disclosure. Furthermore, multifaceted additional functions may advantageously be facilitated and included, said additional functions, in particular, also requiring direct communication with smartphones (in particular by way of programmed apps) or similar portable data appliances. By way of example, these may comprise automatic mapping functions, firmware updates, data post-processing, data preparation, data comparison with other appliances, or the like.

In a further embodiment of the measuring appliance according to the disclosure, the sensor apparatus comprises at least one further sensor from a group of sensors which at least comprises induction sensors, capacitance sensors, ultrasonic sensors, temperature sensors, moisture sensors, radiation sensors, inclination sensors, angle sensors, magnetic field sensors, acceleration sensors and rotational-rate-sensitive sensors.

This allows realization of a further integration of similar and/or complementary measuring instruments in the measuring appliance according to the disclosure. By way of example, the nuclear magnetic resonance sensor may be extended particularly advantageously with induction-sensitive sensors and/or capacitance-sensitive sensors. Preferably, the signals from the further sensors are likewise evaluated by the evaluation apparatus for evaluating the measurement signals supplied by the sensor apparatus. The evaluation results of the various sensors may advantageously be correlated to one another; in particular, measurement values obtained by means of the further sensors may be used to correct and/or optimize and/or calibrate the measurement results ascertained by the nuclear magnetic resonance sensor and/or the measurement results ascertained by the second sensor apparatus. Alternatively, there may also be an output of the further measurement results as a complementary measurement value and/or as a complementary value by means of the output apparatus. By way of example, a drying time of the workpiece under given ambient conditions (temperature and humidity) may be predicted by means of additionally integrated humidity and air temperature sensors.

A method according to the disclosure for nondestructive determination of a material measurement value relating to a material property of a workpiece, in particular in a workpiece, by means of a mobile measuring appliance, in particular by means of a hand-held measuring appliance, is proposed, in which at least one first information item about the material property of the workpiece, in particular moisture present in the workpiece, is obtained by means of at least one first sensor apparatus, in particular a nuclear magnetic resonance sensor, characterized in that at least one further sensor apparatus, in particular based on dielectric and/or resistive methods, is used to obtain at least one second information items about the material property of the workpiece, in particular the moisture present in the workpiece, wherein the first information item is used for optimized actuation of the second sensor apparatus and/or for optimized evaluation of measurement signals supplied by the second sensor apparatus.

In an advantageous configuration of the method according to the disclosure, the first information item obtained by the first sensor apparatus is used to calibrate the second sensor apparatus and/or to calibrate the measurement signals supplied by the second sensor apparatus.

In an advantageous configuration of the method according to the disclosure, at least the information item about the moisture present in the workpiece obtained by means of the first sensor apparatus is used to determine the dry permittivity $\varepsilon_T$ of the workpiece.

In an advantageous configuration of the method according to the disclosure, a parallel and/or quasi-parallel and/or series measurement is carried out with the first sensor apparatus and the second sensor apparatus.

In an advantageous configuration of the method according to the disclosure, the second sensor apparatus uses at least one sensor based on dielectric and/or resistive methods, in particular a capacitance sensor, a microwave sensor, an ultrasonic sensor, a resistance sensor, a conductivity sensor and/or a radar sensor, in particular an ultra-broadband radar sensor and/or a broadband impulse radar sensor.

In particular, the method allows the determination of at least one material measurement value relating to a material property of a workpiece, in particular a moisture measurement value, in particular in a workpiece, wherein the method is characterized by the following essential steps:

generating a first magnetic field in the workpiece by means of a first apparatus, in particular an apparatus arranged in the measuring appliance, generating radiofrequency pulses in the workpiece by means of a second apparatus of the measuring appliance, in particular by means of a radiofrequency coil, detecting at least an amplitude and/or a relaxation time of a measurement signal resulting from the excitation of nuclear spins in the workpiece, in particular by means of an electric current induced in a reception coil and/or an induced electric voltage, extracting Larmor frequencies from a measurement signal, in particular from an electric current induced in a reception coil and/or from an electric voltage induced in a reception coil, determining a material measurement value relating to a material property of a workpiece, in particular an information item relating to the moisture of a workpiece, from the measurement signals of the nuclear magnetic resonance sensor, in particular determining an absolute moisture measurement value and/or a gradient profile of a moisture measurement value into the workpiece, ascertaining the dry permittivity of the workpiece using the information item, generating an electromagnetic signal, in particular an electromagnetic signal penetrating into the workpiece, by means of a second sensor apparatus, in particular a radar signal and/or a microwave signal, detecting reflected electromagnetic signals, evaluating a moisture measurement value, in particular a relative moisture measurement value, in particular with depth resolution into the workpiece, optimizing the actuation of the second sensor apparatus and/or optimizing the evaluation of measurement signals supplied by the second sensor apparatus by means of an information item relating to the moisture of the workpiece obtained by the first sensor apparatus.

BRIEF DESCRIPTION OF THE DRAWINGS

The disclosure is explained in more detail in the subsequent description on the basis of exemplary embodiments depicted in the drawings. The drawing, the description and the claims contain numerous features in combination. Expediently, a person skilled in the art will also consider the features on their own and combine these to give further meaningful combinations. In the figures, the same or similar reference signs denote the same or similar elements.

In detail.

DETAILED DESCRIPTION

Figure 1:
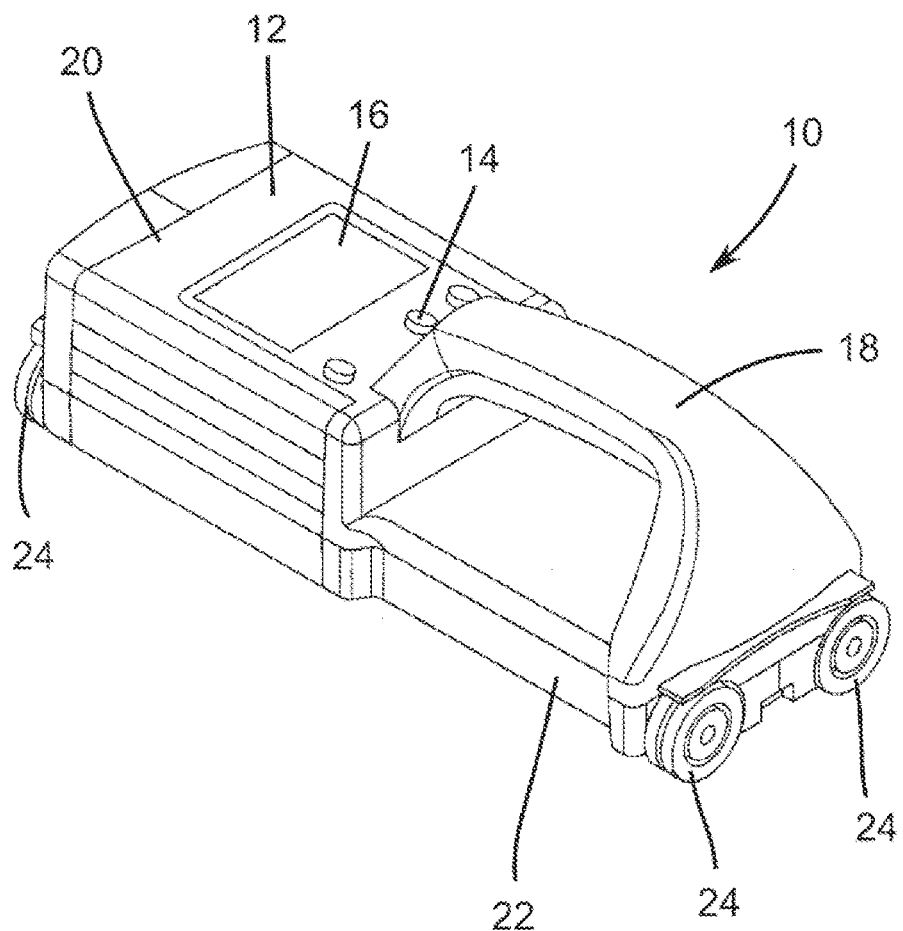
FIG. 1 shows a perspective illustration of a configuration of the mobile measuring appliance according to the disclosure.
Figure 2:
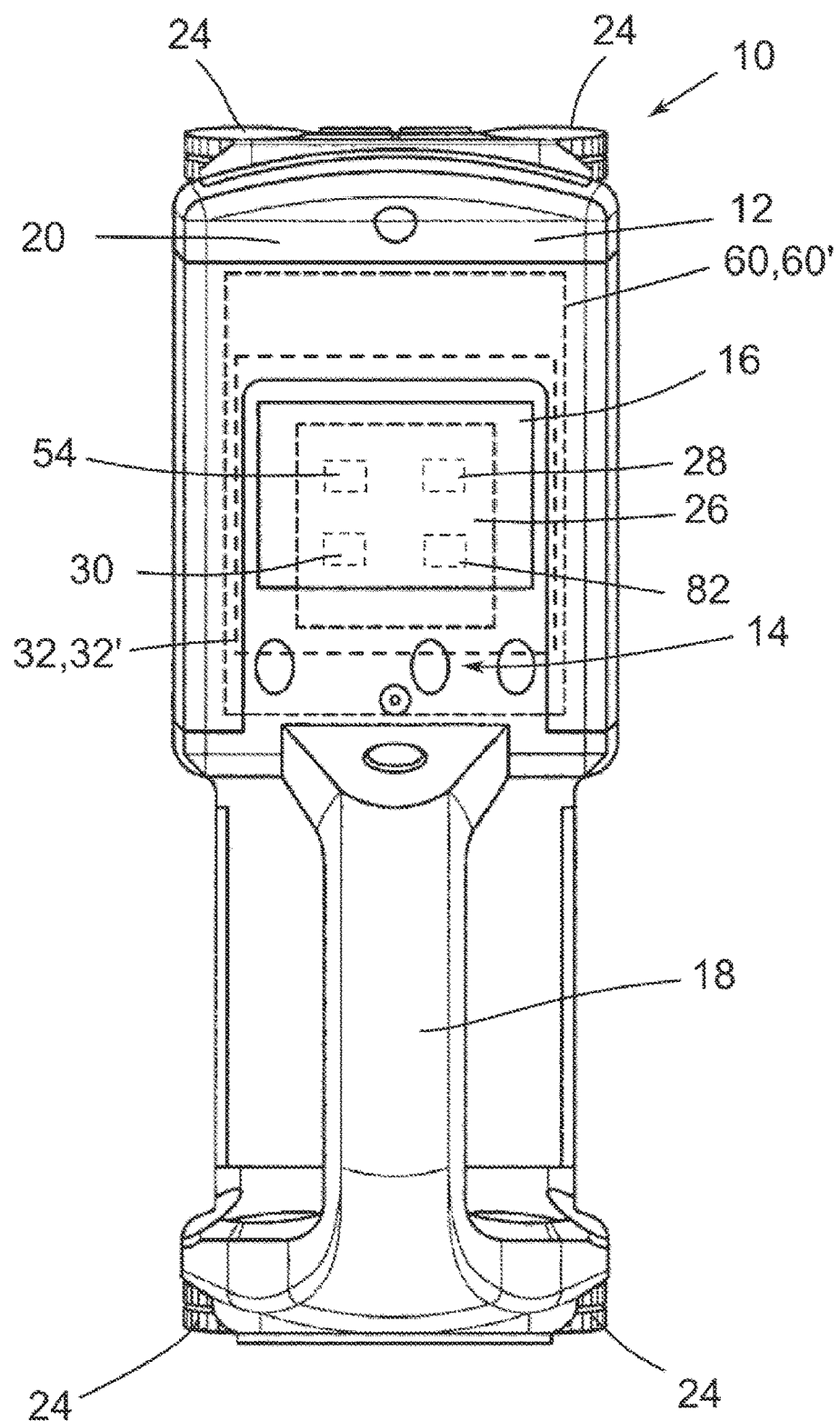
FIG. 2 shows a view of the second housing side of the same configuration of the measuring appliance according to the disclosure.

FIG. 1 and FIG. 2 show two views of an exemplary embodiment of the hand-held measuring appliance 10 according to the disclosure, in a perspective illustration and in a simplified, schematic plan view.

The hand-held measuring appliance 10 embodied in an exemplary manner comprises a housing 12, an input apparatus in the form of actuation elements 14, suitable for switching the hand-held measuring appliance on and off, for starting and configuring a measurement process and for entering working parameters, and an output apparatus in the form of a display 16 for outputting working parameters and/or evaluation results. For transportation purposes and for the guidance thereof, the hand-held measuring appliance 10 comprises a handle 18. The handle 18, the actuation elements 14 and the display are situated on a second housing side 20 of the measuring appliance 10, which typically faces the user when the measuring appliance is operated.

For the purposes of supplying the hand-held measuring appliance 10 with energy, the appliance has a recess on the first housing side 40 (also referred to as rear side of the measuring appliance below) lying opposite to the second housing side 20 on the rear side of the appliance, said recess preferably being provided to receive power-grid-independent energy stores 22, in particular batteries or rechargeable accumulators. The appliance presented in an exemplary manner comprises lithium ion accumulators, the high energy and power density of which is advantageously suitable for supplying the measuring appliance with energy. In an alternative embodiment, the energy store 22 may also be housed in the handle 18 of the measuring appliance 10. Preferably, the apparatus for supplying energy comprises a detachable interlocking and/or force-fit connection interface such that the energy store 22 (in general, also a plurality of energy stores) is (are) arrangeable in a removable and interchangeable manner. Moreover, the energy store 22 may be supplied with energy from a power grid and may be charged within and/or outside of the measuring appliance.

Figure 3:
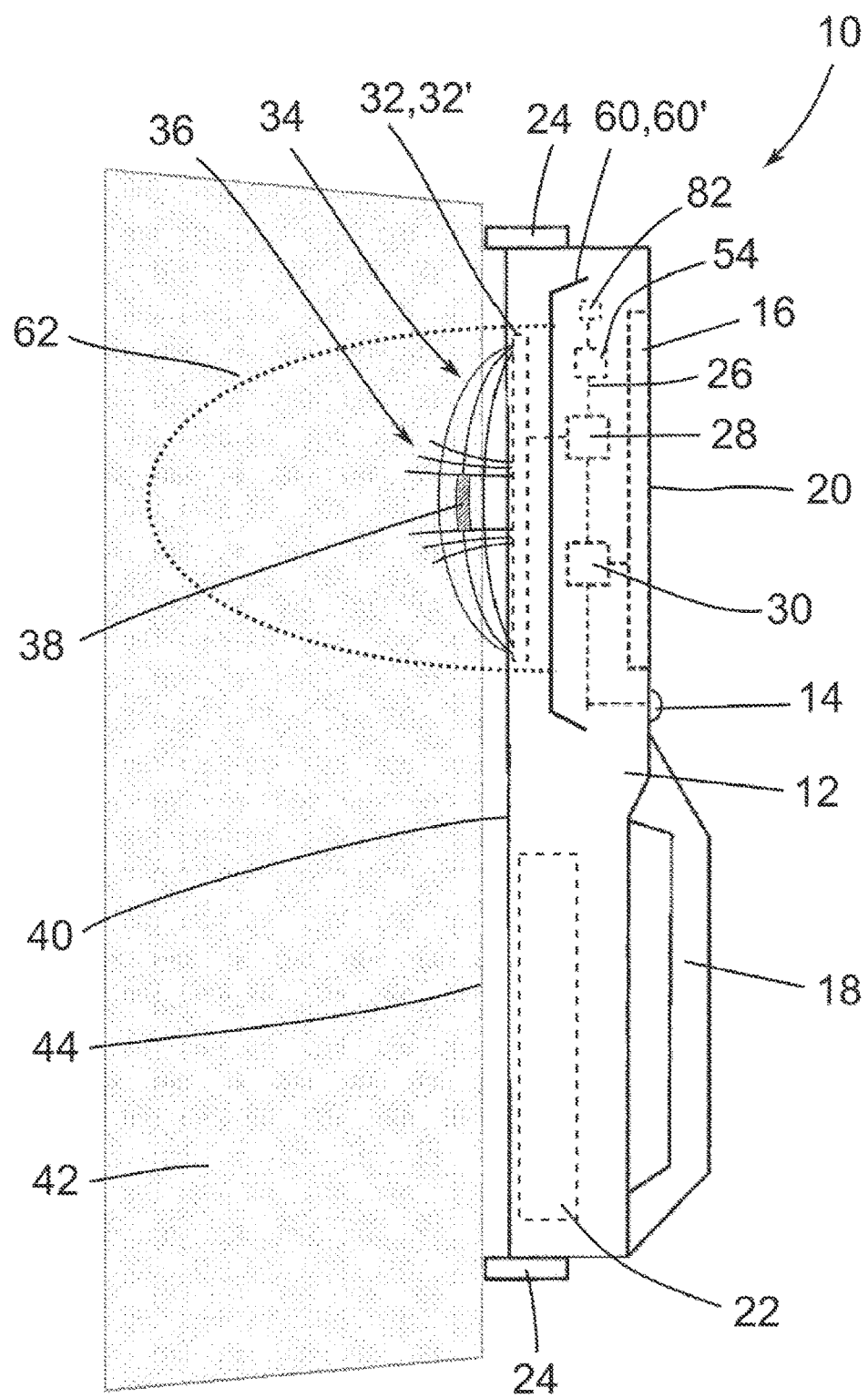
FIG. 3 shows a schematic side view of the same configuration of the measuring appliance according to the disclosure.

A position determination apparatus of the hand-held measuring appliance comprises four wheels 24 in the exemplary embodiment, by means of which the hand-held measuring appliance 10 may be displaced along the surface 44 of a workpiece 42 (cf. FIG. 3). Sensors which are sensitive to rotation of the wheels 24 capture a movement of the measuring appliance 10 and a traveled distance and therefore allow measurement results to be related with a position of the measuring appliance, in particular in relation to the workpiece 42. In an alternative embodiment of the measuring appliance 10, the position determination apparatus may comprise an optical displacement transducer instead of the wheels. Additionally, even more sensors, in particular inclination sensors, angle sensors, translation sensors, acceleration sensors and rotational-rate-sensitive sensors, may be present for determining the position more precisely. After placing the hand-held measuring appliance 10 onto the surface 44 of a workpiece 42 to be measured, for example on a wall or a concrete floor, the change in position of the hand-held measuring appliance as a consequence of displacing the appliance on the workpiece is ascertained. These position data are forwarded to an evaluation apparatus 30 for further evaluation. Particularly advantageously, multidimensional representations of the measurement results, for example, in particular, in the form of a map and/or a pseudo-three-dimensional representation, may be generated by means of the position-dependent measurement and evaluation of a workpiece.

Further components of the measuring appliance 10, in particular a first sensor apparatus 32 comprising a nuclear magnetic resonance sensor 32', a second sensor apparatus 60 comprising an ultra-broadband radar sensor 60', a control apparatus 28 for actuating the first sensor apparatus and the second sensor apparatus, an evaluation apparatus 30 for evaluating at least one measurement signal supplied by the first sensor apparatus and/or the second sensor apparatus, and a data communication interface 54 connected to the control and/or evaluation apparatus, are housed on a carrier element 26, in particular on a system circuit board or printed circuit board within the housing 12 (see, in particular, FIG. 2).

The control apparatus 28 has control electronics comprising means for communicating with the other components of the measuring appliance, for example means for open-loop and/or closed-loop control of the first sensor apparatus and the second sensor apparatus and means for open-loop control of the measuring appliance. In particular, the control apparatus 28 comprises a unit with a processor unit, a memory unit and an operating program stored in the memory unit. The control apparatus 28 is provided to adjust at least one operating functional parameter of the measuring appliance depending on at least one input by the user, via the evaluation apparatus and/or via the data communication interface 54.

Figure 4:
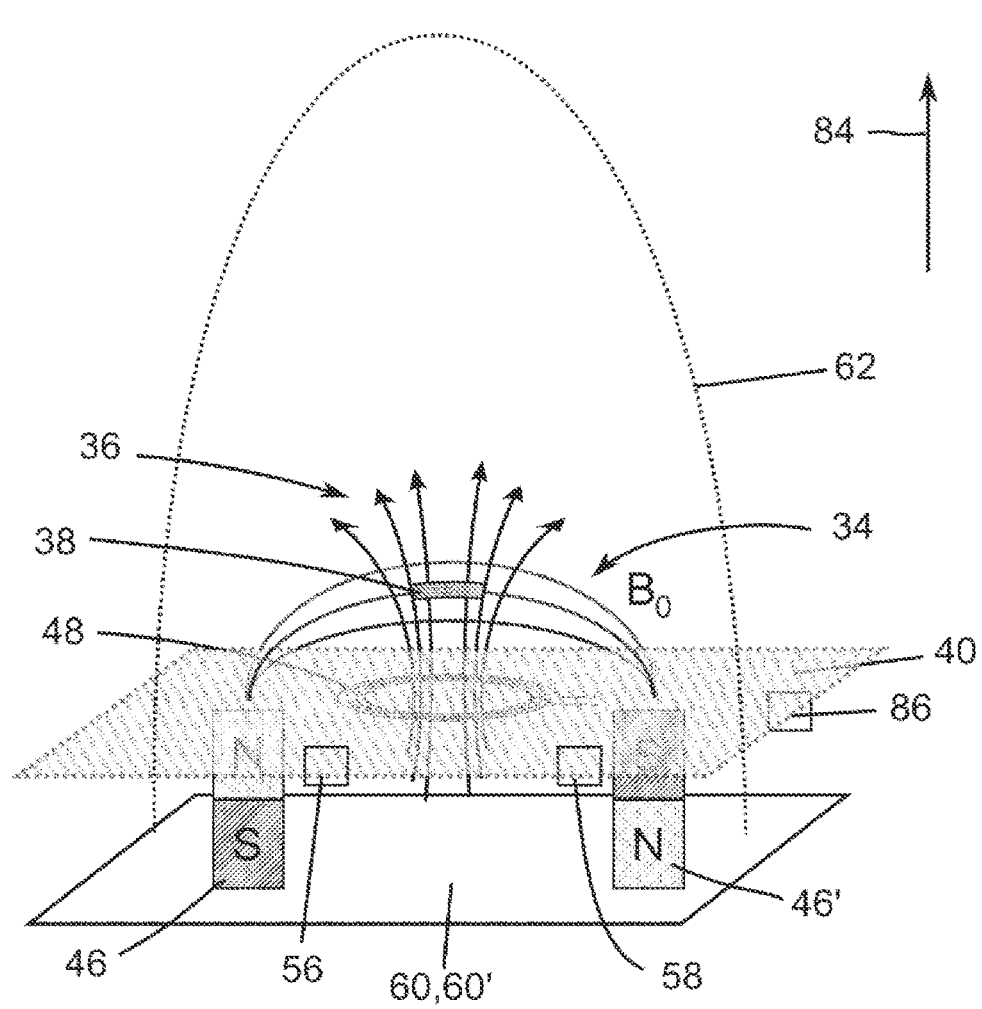
FIG. 4 shows a schematic and simplified illustration of an embodiment of the components forming the first sensor apparatus and the second sensor apparatus, and the electromagnetic fields generated therewith.

The nuclear magnetic resonance sensor 32', which is explained in more detail in FIG. 4, is provided for exciting nuclear magnetic resonance of nuclear spins of atomic nuclei in the material of the workpiece 42. According to the disclosure, the measured resonance signal is used at least for the nondestructive determination of a moisture measurement value of the workpiece, in particular in accordance with the measurement depth of the sensor for determining a moisture measurement value in the workpiece 42, i.e. for ascertaining information items which, inter alia, relate to a relative and/or absolute moisture content, a moisture gradient into the workpiece, binding states of the water forming the moisture and/or time-dynamic processes of the water forming the moisture. Here, the measurement depth is in particular down to 1 cm, advantageously down to 2 cm, particularly advantageously down to 3 cm into the workpiece. The nuclear magnetic resonance signal of the nuclear spins of the atomic nuclei excited in the material of the workpiece 42 is detected by means of a reception coil of the nuclear magnetic resonance sensor 32'. The generated measurement signal, in particular the amplitude and/or relaxation times thereof, is forwarded to the evaluation apparatus 30, by means of which it is evaluated and prepared by means of evaluation routines and forwarded to an output apparatus 16 and/or the control apparatus 28 and/or a data communication interface 54.

The ultra-broadband radar sensor 60' is advantageously used to emit an electromagnetic signal which penetrates deep into the material of the workpiece 42, the workpiece-internal reflections and/or scattering of said signal being measured by the sensor. A measurement signal generated by this sensor is evaluated by the evaluation apparatus 30, and so a moisture measurement value, in particular depth-resolved moisture measurement values, is/are obtained. In particular, the measurement depth of the ultra-broadband radar sensor 60' is down to 10 cm, advantageously down to 15 cm and particularly advantageously more than 15 cm.

The evaluation apparatus 30 for evaluating at least one measurement signal supplied by the first sensor apparatus and/or the second sensor apparatus, optionally also for evaluating measurement signals from further sensor apparatuses of the hand-held measuring appliance 10, comprises, in particular, an information input, information processing and an information output. Advantageously, the evaluation apparatus 30 consists at least of a processor and a memory with an executable operating program stored thereon, and allows evaluation of at least a measurement signal of the nuclear magnetic resonance sensor 32' and/or a measurement signal of the ultra-broadband radar sensor 60' and determination of moisture measurement values in relation to the workpiece. Particularly advantageously, the evaluation apparatus has stored correction tables and/or calibration tables, which render it possible to interpret, convert, interpolate and/or extrapolate the evaluation results and calibrate the measuring appliance, in particular the evaluation routines, in respect of a workpiece material.

According to the disclosure, an information item relating to the moisture of the workpiece, obtained by means of the nuclear magnetic resonance sensor 32', may be used to influence, preferably optimize, particularly preferably calibrate the evaluation of a measurement signal supplied by the ultra-broadband radar sensor 60'. As a result of this, an evaluation of measurement signals supplied by the second sensor apparatus which is adapted to the conditions of the workpiece and hence optimized may be facilitated. Hence, it is particularly advantageously possible to relate relative moisture measurement values from the ultra-broadband radar sensor 60' directly to absolute moisture measurement values which are measured by means of the nuclear magnetic resonance sensor, and hence absolute moisture measurement values up to a maximum measurement depth corresponding to the maximum measurement depth of the ultra-broadband radar sensor 60' are obtained (cf. FIG. 5).

Furthermore, an information item relating to the moisture of the workpiece, obtained by means of the nuclear magnetic resonance sensor 32', may be used to realize an optimized actuation of the second sensor apparatus, in particular of the ultra-broadband radar sensor 60', by way of the control apparatus. By way of example, physical and/or technical control parameters and characteristics such as voltages, currents, pulse durations, powers, emission directions of the ultra-broadband radar sensor 60' may be subject to closed-loop and/or open-loop control depending on the information item.

The evaluation results are output by the evaluation apparatus 30 for further use via the control apparatus 28, either for transmitting the data to the data communication interface 54 or directly to a user of the measuring appliance 10. In particular, an output to a user may be effected by means of illustration on the display 16. The output on the display 16 may be carried out graphically, numerically and/or alphanumerically, for example in the form of a measurement value, a measurement curve, a signal profile, a time profile, as image data or in a gradient representation and in a combination thereof. Alternatively or additionally, a representation by means of a signal indication is possible, in particular by way of e.g. a light-emitting diode which evaluates a target variable, for example by way of color coding (e.g. red, yellow, green).

For the purposes of determining a moisture measurement value of a workpiece, in particular in a workpiece, the measuring appliance 10 is positioned with the first housing side 40 thereof, i.e. with the appliance rear side, in a planar fashion in the immediate vicinity of the workpiece 42, in particular contacting the surface 44 of the latter. In the process, the magnetic fields 34, 36 generated by the nuclear magnetic resonance sensor 32' and the electromagnetic radiation of the ultra-broadband radar sensor 60' emerge through the first housing side 40 from the measuring appliance 10 and penetrate into the workpiece 42, with the first sensitive region 38 and the second sensitive region 62 coming to rest in the workpiece (see, in particular, FIG. 3). Positioning the measuring appliance 10 in the immediate vicinity of the workpiece surface 44 facilitates determining absolute moisture measurement values, in particular up to 10 cm, advantageously up to 15 cm and particularly advantageously more than 15 cm, into the workpiece 42.

FIG. 3 depicts the embodiment according to the disclosure of the hand-held measuring appliance 10 from FIGS. 1 and 2 in a simplified schematic side view. The nuclear magnetic resonance sensor 32' comprises two apparatuses for generating magnetic fields, in particular a permanent magnet arrangement 46, 46' (cf. FIG. 4) which generates a first magnetic field 34 and a radiofrequency coil 48 (cf. FIG. 4) which generates a second magnetic field 36. The nuclear magnetic resonance sensor 32' is configured in such a way that the first magnetic field 34 is aligned substantially parallel to the first housing side 40 while the second magnetic field 36 is aligned substantially perpendicular to the magnetic field lines of the first magnetic field 34. The two magnetic fields superpose in an extended region, in which, in particular, the sensitive region 38 of the nuclear magnetic resonance sensor 32' is situated as well, in particular as a layer-shaped region.

The ultra-broadband radar sensor 60', which is provided for emitting electromagnetic radiation and for detecting signals reflected and/or scattered in the interior of the workpiece, has a second sensitive region 62 which is identical with the solid angle of the maximum sensitivity of the sensor (direction of extent). The second sensitive region 62 extends symmetrically with respect to a perpendicular in relation to the first housing side of the measuring appliance, along which the first sensitive region 38 of the nuclear magnetic resonance sensor 32' may advantageously be displaced as well.

With the first housing side 40, the hand-held measuring appliance 10 is positioned in such a way in the immediate vicinity of a workpiece 42 to be examined that the distance between the first housing side 40 and the workpiece surface 44 is minimized. What this achieves is that the magnetic fields 34, 36 of the nuclear magnetic resonance sensor 32' and the electromagnetic radiation of the ultra-broadband radar sensor 60' penetrate into the workpiece and the first sensitive region 38 and the second sensitive region 62 come to rest in the workpiece 42.

By varying the second magnetic field 36 generated by the second apparatus, i.e., in particular, by varying the radiofrequency coil 48 and/or varying the frequency and/or varying the current and/or varying the voltage in the radiofrequency coil 48, it is possible to vary the first sensitive region 38 in terms of its distance from the first housing side 40 and hence modify the distance of the sensitive region 38 in the workpiece from the surface 44 thereof. Alternatively and/or additionally, the nuclear magnetic resonance sensor 32' may be repositioned, in particular repositioned mechanically, in the housing 12 of the hand-held measuring appliance 10 in such a way that the distance between the nuclear magnetic resonance sensor 32' and the first housing side 40 is varied and consequently the distance of the first sensitive region 38 in the workpiece 42 from the surface 44 of the latter is also varied. Depth profiles of the moisture measurement values may be created particularly advantageously in this manner.

According to the disclosure, an information item relating to the moisture of the workpiece, obtained by means of the nuclear magnetic resonance sensor, may be used to influence, preferably optimize, particularly preferably calibrate the evaluation of a measurement signal supplied by the ultra-broadband radar sensor 60'. As a result of this, an evaluation of measurement signals supplied by the second sensor apparatus 60 which is adapted to the conditions of the workpiece and hence optimized may be facilitated. Hence, it is particularly advantageously possible to relate relative moisture measurement values from the ultra-broadband radar sensor 60' directly to absolute moisture measurement values which are measured by means of the nuclear magnetic resonance sensor 32', and hence absolute moisture measurement values up to a maximum measurement depth corresponding to the maximum measurement depth of the ultra-broadband radar sensor 60' are obtained (cf. FIG. 5).

FIG. 4 depicts the components of an embodiment of the nuclear magnetic resonance sensor 32' according to the disclosure and of the ultra-broadband radar sensor 60' in a simplified and schematic illustration. Two permanent magnets 46, 46' which are arranged perpendicular to the first housing side 40 and antiparallel in relation to one another generate a first magnetic field 34, in particular a static magnetic field, which extends substantially parallel to the surface of the first housing side 40. This first magnetic field provided for aligning the nuclear spins of the atomic nuclei present in the material sample has, for example, in particular, a magnetic field strength of 0.5 tesla, with the permanent magnets being produced from a neodymium iron boron alloy. In this exemplary embodiment, the second apparatus for generating the second magnetic field is formed by a radiofrequency coil 48. As soon as current flows through this coil, an electromagnetic field, in particular the second magnetic field 36, is generated. The two magnetic fields superpose in a region which lies substantially outside of the housing 12 of the measuring appliance 10. The sensitive region 38 of the nuclear magnetic resonance sensor 32' likewise lies in the superposition field of the magnetic fields 34 and 36. Depending on the frequency of the radiated-in electromagnetic field 36 and the static magnetic field strength of the first magnetic field 34, the sensitive region is defined by an area in an ideal case, in which the magnetic field strength of the first magnetic field 34 is constant and, in particular, has a defined magnitude. In reality, the area in fact has a layered shape on account of non-exact frequencies. Since the magnetic field lines 34 do not extend exactly parallel to the first housing side 40, the sensitive region 38 is therefore also curved in a manner corresponding to the magnetic field lines as a consequence thereof. The curvature and form of the first magnetic field 34, and hence of the sensitive region 38, may be influenced and, in particular, homogenized using further means, for example a shim coil 56 and/or magnetic shielding 58.

The ultra-broadband radar sensor 60' is depicted as an electrically conductive surface, in particular depicted as a metal sheet. The second sensitive region 62 of the ultra-broadband radar sensor 60' corresponds to the chief emission direction of the sensor and therefore spans an emission cone which may penetrate deep into the workpiece in the case of suitable positioning of the measuring appliance.

Figure 5:
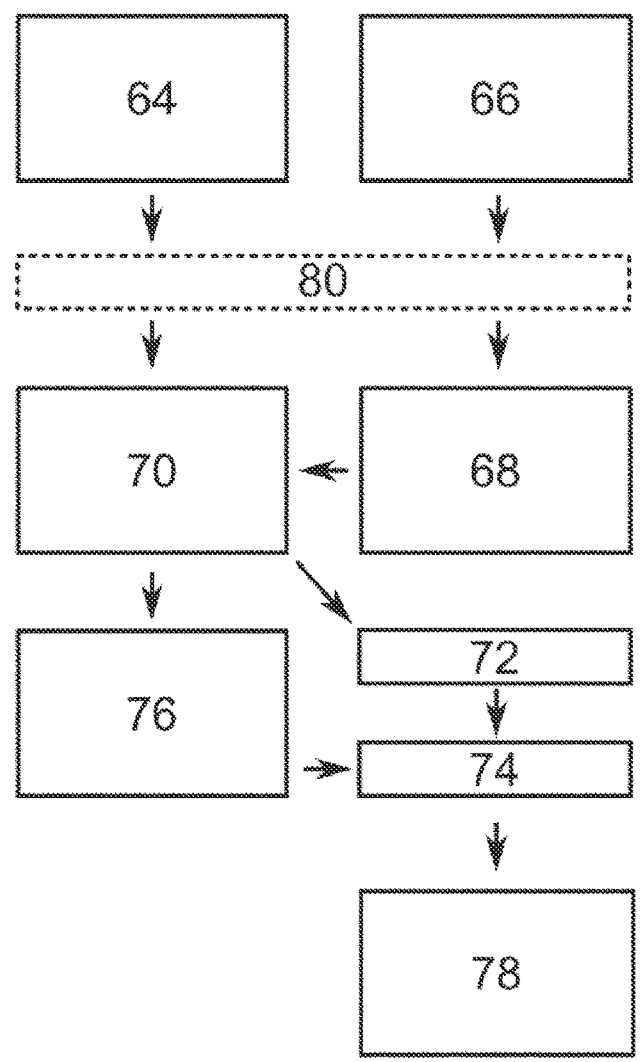
FIG. 5 shows a schematic illustration of a measurement method of the measuring appliance according to the disclosure.

FIG. 5 schematically depicts a possible measurement process using the measuring appliance according to the disclosure. Starting with the measurement by the nuclear magnetic resonance sensor 32' in step 64, volume components $V_m$ of the water forming the moisture are ascertained as a function $F_1$ of the measurement depth $z_m$ of the discrete layers m=1 . . . a in the workpiece for various measurement depths $z_m$ (m=1 . . . a) into the workpiece up to the maximum measurement depth $z_a$ of the nuclear magnetic resonance sensor:

$$V_{1...a} = F_1(z_{1...a}) \quad (1)$$

The second sensor apparatus 60, here using the example of a radar sensor 60', allows measurement signals $SI_{1...b}$ to be measured in the workpiece up to the maximum measurement depth $$z_b = \sum_{m=1}^{b} d_m$$

or the radar sensor, depicted in step 66. In the special case where $d_m$ is constant for various m, the maximum measurement depth may be simplified to $z_b = b \cdot d_m$. The measurement signal $SI_{1...b}$ substantially depends (functional relationship $F_2$) on the radar frequency f, the layer thicknesses $d_m$ and the complex-valued effective material permittivities $\varepsilon_{eff,m}$ thereof ($V_m$, $d_m$, $\varepsilon_{eff,m}$, etc. represent parameters of in each case a single layer):

$$SI_{1...b} = F_2(f, d_{1...b}, \varepsilon_{eff,1...b}) = F_3(f, d_{1...b}, \varepsilon_T, \varepsilon_{water}, V_{1...b}) = F_4(d_{1...b}). \quad (2)$$

Alternatively, the measurement signal may also be expressed as a function ($F_3$) of the radar frequency f, the layer thicknesses $d_m$, the dry permittivity $\varepsilon_T$ of the material of the workpiece, the permittivity $\varepsilon_{water}$ and the volume component $V_m$ of the water forming the moisture at the corresponding measurement depth.

The signal $SI_{1...b}$ can be split into signal components $SI_{1...a}$ and $SI_{a+1...b}$, with the latter signal component originating from layers beyond the maximum measurement depth $z_a$ of the nuclear magnetic resonance sensor 32' (step 68):

$$SI_{1...b} = F(SI_{1...a} + SI_{a+1...b}). \quad (3)$$

By setting the signal components $SI_{a+1...b}$ beyond the measurement depth of the nuclear magnetic resonance sensor 32' to zero or by directly determining the surface-near reflection $SI_{1...a}$ (for example by modeling the measurement data), it is possible to correlate the measurement values from the nuclear magnetic resonance sensor 32' and those from the radar sensor 60' for the measurement depth up to $z_a$ and determine the dry permittivity $\varepsilon_T$ in step 70:

$$\varepsilon_{eff,1...a}^{\alpha} = \left(1 - V_{1...a} - \sum_{i=1}^{n} V_i'\right) \cdot \varepsilon_T^{\alpha} + V_{1...a} \cdot \varepsilon_{1...a}^{\alpha} + \sum_{i=1}^{n} V_i' \varepsilon_i^{\alpha}. \quad (4)$$

Here, $V_i'$ and $\varepsilon_i$ represent volume components and permittivities of further substance components in the material of the workpiece, for example capillary water, air inclusions, etc. The parameter α is determined by an underlying model.

If the dry permittivity $\varepsilon_T$ is known, the signal component $SI_{a+1...b}$ of the deeper layers may be evaluated in respect of volume component of the water of the moisture (step 72).

If the material density ρ is known, the volume components of the water of the moisture may be converted into mass components in step 74. The material density may emerge either by the user specifying the material of the workpiece or, alternatively, from a measurement using the nuclear magnetic resonance sensor 32' in step 76 as well. Finally, the ascertained measurement values are output to the user (step 78), for example by means of a display 16, an LED, a color scale or via a data appliance, in particular a smartphone, connected wirelessly to the measuring appliance.

If the material is specified by the user, it is further possible to carry out corrections and/or calibrations of the measurement signals from the nuclear magnetic resonance sensor 32' and/or from the radar sensor 60' in step 80. By way of example, contributions of organic constituents of the workpiece to the measurement signals of the water forming the moisture may be taken into account by way of calibration tables.

Alternatively, it is possible to provide an appliance-internal calibration function, by means of which relevant parameters, in particular, for example, the dry permittivity, may be measured if a dry workpiece is present and stored in the appliance for further use such that a calibration of the measurement signals from the nuclear magnetic resonance sensor 32' may be undertaken in step 80.

Furthermore, calibration data for calibrating the measurement signals or the evaluation thereof in step 80 may be obtained by inputting material parameters, in particular a layer sequence of the material building up the workpiece. Alternatively or additionally, these calibration data may also be derived from measurement signals from the nuclear magnetic resonance sensor 32' or from the radar sensor 60' in step 80.

The invention claimed is:

1. A mobile measuring appliance for nondestructive determination of a material measurement value relating to a material property of a workpiece, comprising:
   a housing;
   a first sensor apparatus at least partially located in the housing;
   a second sensor apparatus at least partially located in the housing;
   a control apparatus configured to actuate the first sensor apparatus and/or the second sensor apparatus;
   an evaluation apparatus configured to evaluate at least one measurement signal supplied by the first sensor apparatus and/or the second sensor apparatus; and
   an apparatus for supplying energy to the measuring appliance,
   wherein the first sensor apparatus comprises at least one nuclear magnetic resonance sensor and the second sensor apparatus comprises at least one sensor based on dielectric and/or resistive methods,
   wherein an information item about the material property of the workpiece is obtained by evaluating the at least one measurement signal supplied by the first sensor apparatus, and
   wherein said information item is configured to optimize actuation of the second sensor apparatus and/or to optimize evaluation of the at least one measurement signal supplied by the second sensor apparatus.

2. The measuring appliance as claimed in claim 1, wherein:
   the at least one sensor of the second sensor apparatus is selected from the group consisting of capacitance sensors, microwave sensors, ultrasonic sensors, resistance sensors, conductivity sensors, ultra-broadband radar sensors, and broadband impulse radar sensors.

3. The measuring appliance as claimed in claim 1, wherein:
the nuclear magnetic resonance sensor comprises a first apparatus configured to generate a first magnetic field, a second apparatus configured to generate a second magnetic field, the second magnetic field superimposing the first magnetic field,
the control apparatus comprises at least one control unit configured to control the second apparatus, and
the control unit is configured to modify the second magnetic field to generate pulse sequences.

4. The measuring appliance as claimed in claim 3, wherein:
the first and second magnetic fields of the nuclear magnetic resonance sensor define a first sensitive region of the nuclear magnetic resonance sensor, and
the first sensitive region is a layer-shaped region extending substantially parallel to and at a distance from a first housing side outside of the housing of the measuring appliance.

5. The measuring appliance as claimed in claim 4, wherein the first sensitive region of the nuclear magnetic resonance sensor is displaceable outside of the housing perpendicularly to the first housing side of the measuring appliance by 1 cm to 3 cm.

6. The measuring appliance as claimed in claim 4, wherein the second sensor apparatus has a second sensitive region extending substantially symmetrically in relation to a perpendicular to the first housing side of the measuring appliance along said perpendicular.

7. The measuring appliance as claimed in claim 6, further comprising:
an influencing device configured to influence a direction of extent and/or a homogeneity and/or a geometry of the first sensitive region and/or of the second sensitive region.

8. The measuring appliance as claimed in claim 4, further comprising:
an input apparatus configured to input working parameters and arranged in or on a second housing side of the measuring appliance.

9. The measuring appliance as claimed in claim 8, further comprising:
an output apparatus configured to output working parameters and/or evaluation results and arranged in a second housing side of the measuring appliance.

10. The measuring appliance as claimed in claim 9, wherein:
the first housing side of the measuring appliance lies opposite the second housing side,
the second housing side is configured to receive the input apparatus and/or the output apparatus, and
the second housing side is arranged on a rear side of the measuring appliance.

11. The measuring appliance as claimed in claim 9, wherein the control apparatus has an operating mode in which output parameters of the output apparatus are specified and/or are made available to the measuring appliance.

12. The measuring appliance as claimed in claim 1, wherein:
the nuclear magnetic resonance sensor comprises a detecting apparatus configured to detect a magnetic field change, and
the detecting apparatus includes a reception coil configured to detect the magnetic field change.

13. The measuring appliance as claimed in claim 1, further comprising:
a shielding device configured to minimize mutual interference influences among the sensor apparatuses.

14. The measuring appliance as claimed in claim 1, wherein the evaluation apparatus is configured to evaluate the at least one measurement signal to determine:
a relative and/or absolute moisture content;
a moisture gradient into the workpiece;
binding states of the water forming the moisture;
time-dynamic processes of the water forming the moisture; and/or
further structurally relevant parameters including salt content, composition, density, and porosity of the material of the workpiece.

15. The measuring appliance as claimed in claim 1, wherein the control apparatus has an operating mode in which specifications relating to the workpiece are specified by user inputs and/or are made available to the measuring appliance.

16. A method for nondestructive determination of a material measurement value relating to a material property of a workpiece with a mobile measuring appliance, the method comprising:
obtaining at least one first information item about the material property of the workpiece with at least one first sensor apparatus including a nuclear magnetic resonance sensor;
obtaining at least one second information item about the material property of the workpiece using at least one further sensor apparatus of the mobile measuring appliance, the at least one further sensor apparatus based on dielectric and/or resistive methods; and
optimizing actuation of the second sensor apparatus and/or optimizing evaluation of measurement signals supplied by the second sensor apparatus based on the first information item.

17. The method as claimed in claim 16, further comprising:
calibrating the second sensor apparatus and/or calibrating the measurement signals supplied by the second sensor apparatus based on the first information item obtained by the first sensor apparatus.

18. The method as claimed in claim 16, wherein the at least one first information item obtained with the first sensor apparatus is based on a moisture present in the workpiece, and the method further comprises:
determining the dry permittivity of the workpiece with the at least one first information item.

19. The method as claimed in claim 16, further comprising:
carrying out a parallel and/or quasi-parallel and/or series measurement with the first sensor apparatus and the second sensor apparatus.

20. The method as claimed in claim 16, wherein the second sensor apparatus uses at least one sensor based on dielectric and/or resistive methods selected from the group consisting of capacitance sensors, microwave sensors, ultrasonic sensors, resistance sensors, conductivity sensors, ultrabroadband radar sensors, and broadband impulse radar sensors.

* * * * *